United States Patent
Eskuri et al.

(10) Patent No.: US 7,001,406 B2
(45) Date of Patent: Feb. 21, 2006

(54) CARTRIDGE EMBOLIC PROTECTION FILTER AND METHODS OF USE

(75) Inventors: Alan Eskuri, Hanover, MN (US); James G. Hansen, Coon Rapids, MN (US)

(73) Assignee: SciMed Life Systems Inc., Maple Grove, MN (US)

( * ) Notice: Subject to any disclaimer, the term of this patent is extended or adjusted under 35 U.S.C. 154(b) by 561 days.

(21) Appl. No.: 10/154,739

(22) Filed: May 23, 2002

(65) Prior Publication Data

US 2003/0220665 A1 Nov. 27, 2003

(51) Int. Cl.
*A61M 29/00* (2006.01)

(52) U.S. Cl. .................................................. 606/200
(58) Field of Classification Search ................ 606/200
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |

(Continued)

FOREIGN PATENT DOCUMENTS

DE  28 21 048  7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner*—(Jackie) Tan-Uyen T. Ho
(74) *Attorney, Agent, or Firm*—Crompton, Seager & Tufte LLC

(57) ABSTRACT

An embolic protection filter having a reduced profile for placement within a body lumen is disclosed. One embodiment has an embolic protection filter that includes a filter frame slidably and rotationally disposed along a guidewire, a plurality of retaining collars coupled to a proximal end of the filter frame, a plurality of expandable struts each having a proximal section adapted to slide within a corresponding retaining collar, and a filter mesh coupled to a distal section of the expandable struts for filtering embolic debris.

39 Claims, 1 Drawing Sheet

U.S. PATENT DOCUMENTS

| | | |
|---|---|---|
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnic et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,336,934 B1 | 1/2002 | Gilson et al. |
| 6,344,049 B1 | 2/2002 | Levinson et al. |
| 6,371,971 B1 * | 4/2002 | Tsugita et al. .............. 606/200 |
| 6,793,666 B1 * | 9/2004 | Hansen et al. .............. 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 296 605 A1 | 12/1988 |
| EP | 0 411 118 A1 | 2/1991 |
| EP | 0 472 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |

| | | |
|---|---|---|
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 02/32496 A1 | 4/2002 |
| WO | WO 02/40090 A1 | 5/2002 |

OTHER PUBLICATIONS

"Endovascular Grafts, Stents Drive Interventional Radiology Growth," *Cardiovascular* Device Update, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Cartoid Interventions," *J. Endovasc. Surg.*, 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ", American Heart Journal, 125(2 Pt 1):362-366 (Feb. 1993).

Mazur et al., "Directional Atherectomy with the Omnicath™: A Unique Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," Rinsho Kyobu Geka, 14(2): English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common after Directional Atherectomy . . . ," American Heart Journal, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

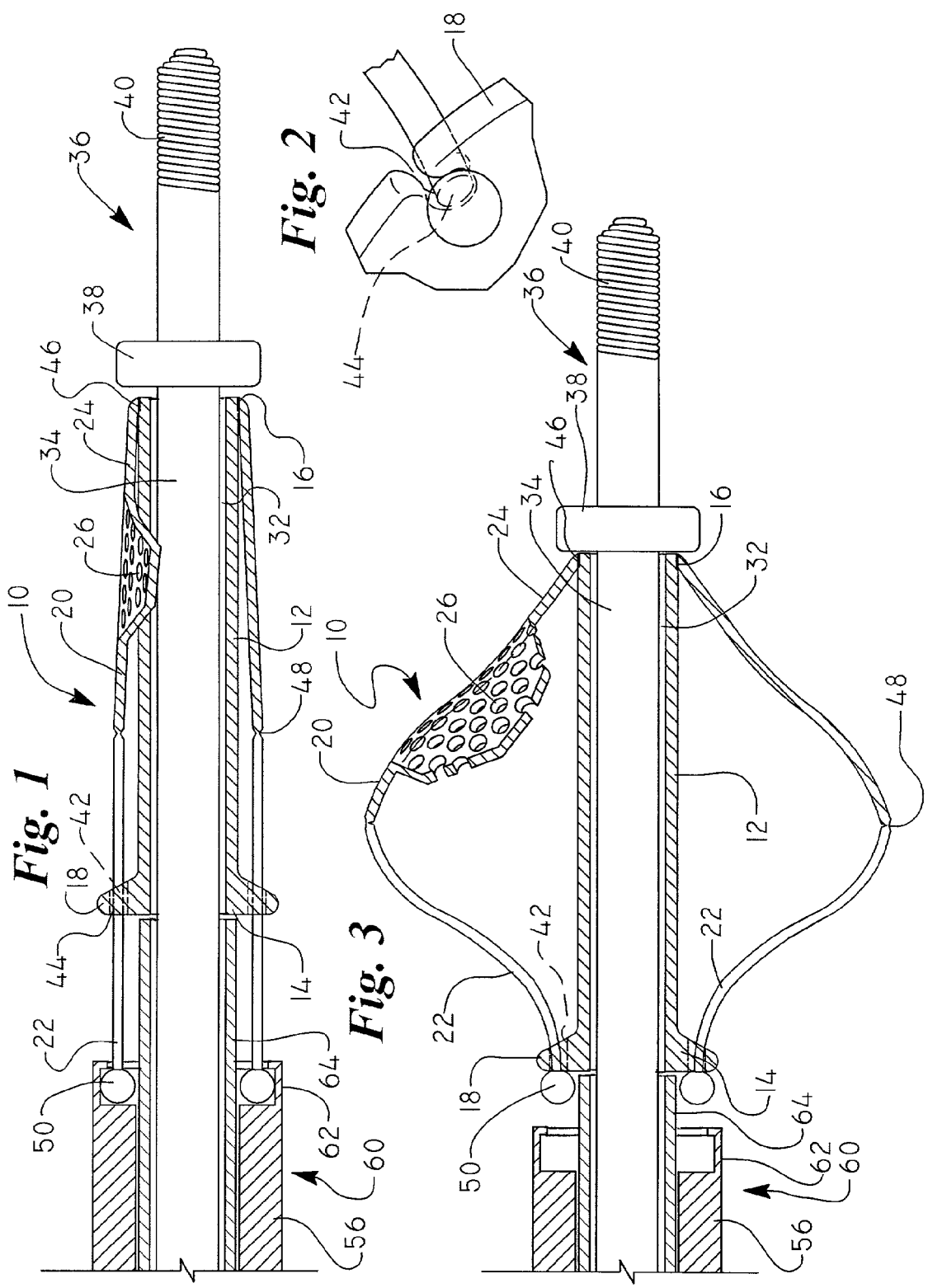

CARTRIDGE EMBOLIC PROTECTION FILTER AND METHODS OF USE

FIELD OF THE INVENTION

The present invention relates generally to the field of embolic protection devices. More specifically, the present invention pertains to cartridge embolic protection filters having a reduced profile.

BACKGROUND OF THE INVENTION

Embolic protection filters are frequently used in conjunction with other therapeutic devices to filter embolic material such as plaque or thrombus from the blood stream. In a typical application such as percutaneous transluminal angioplasty (PTA) or percutaneous transluminal coronary angioplasty (PTCA), a collapsed filter is advanced along a guidewire to a location distal a lesion to be dilated. After the filter has been positioned and deployed within the vessel, an angioplasty catheter containing an angioplasty balloon is advanced along the guidewire and positioned proximal the lesion. The angioplasty balloon is then inflated, forcing the embolic material to become dislodged from the walls of the vessel and flow downstream, where it is collected by the filter. At the conclusion of the procedure, the guidewire, catheter, filter, and collected embolic debris are then removed from the body.

Catheters are frequently utilized in advancing and removing embolic protection filters within the body. These catheters often require relatively large chambers to transport the collapsed filter within the body, resulting in an enlarged profile. This enlarged profile may hinder placement of the device within the tortuous vasculature. In some cases, the delivery catheter may even aggravate the lesion to be dilated. As such, it is desireable to have an embolic protection filter with a compact profile to facilitate transport within the body.

SUMMARY OF THE INVENTION

The present invention relates generally to the field of embolic protection devices. More specifically, the present invention pertains to cartridge embolic protection filters having a reduced profile. In one embodiment of the present invention, an embolic protection filter comprises a filter frame slidably and rotationally disposed along a guidewire, a plurality of retaining collars coupled to the proximal end of the filter frame, a plurality of expandable struts each having a proximal portion adapted to slide within a corresponding retaining collar, and a filter mesh coupled to the expandable struts for filtering embolic debris. The expandable struts are biased to radially expand from a collapsed, radially compact position to an open, radially expanded position, when actuated.

To actuate the expandable struts between the collapsed (i.e. radially compact) position) and the open (i.e. radially expanded) position, an actuator mechanism is used. In one implementation of the present invention, an actuator mechanism comprises a tubular member having a channel on a distal end adapted to releasably lock onto a proximal section of the expandable struts. In another implementation of the present invention, an actuator mechanism comprises a tubular member having a threaded portion on a distal end adapted to engage a corresponding threaded surface disposed on a proximal section of the expandable struts.

In use, an advancing member is used to advance the actuator mechanism and collapsed filter along the guidewire distal a lesion. Once in place, the actuator mechanism is disengaged from the expandable struts, allowing the expandable struts to radially deploy within the vessel. To retrieve the embolic protection filter, the actuator mechanism is advanced distally along the guidewire until the distal end of the mechanism re-attaches to the expandable struts. Once attached, the operator retracts the actuator mechanism proximally, causing the expandable struts to radially collapse. The actuator, advancing member, and collapsed filter containing the collected embolic debris are then removed from the body.

BRIEF DESCRIPTION OF THE DRAWINGS

FIG. 1 is a cross-sectional view of an embolic protection filter in accordance with an embodiment of the present invention showing the filter in an closed, radially compact position;

FIG. 2 is a perspective view of the collar illustrated FIG. 1; and

FIG. 3 is a cross-sectional view of the embolic protection filter of FIG. 1, showing the filter in an open, radially expanded position.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, materials and manufacturing processes are illustrated for the various elements, those skilled in the art will recognize that many of the examples provided have suitable alternatives that may be utilized.

FIG. 1 is a cross-sectional view of an embolic protection filter 10 in accordance with an exemplary embodiment of the present invention. Embolic protection filter 10 includes a filter frame 12, a plurality of retaining collars 18, a plurality of expandable struts 20, and a filter mesh 26 attached to a distal section 24 of the expandable struts 20. The expandable struts 20, which are discussed in greater detail below, are biased to move between a collapsed, radially compact position, and an open, radially expanded position, when actuated.

Filter frame 12 defines a tubular member having a proximal end 14, a distal end 16, and a guidewire lumen 32. In a preferred application, filter frame 12 is slidably and rotationally disposable along a guidewire 34. Guidewire 34 has a proximal end (not shown), a distal end 36, and a distal stop 38 fixedly attached at or near distal end 36 thereof. Spring tip 40 can be placed on the distal end 36 of guidewire 34 to aid in navigating the guidewire 34 through the body.

Disposed about the proximal end 14 of filter frame 12 are a plurality of retaining collars 18. As shown in greater detail in FIG. 2, each of the retaining collars 18 defines a lumen 42 extending distally from an opening 44. In one implementation of the present invention, the retaining collars 18 and filter frame 12 are formed together from a single material (e.g. polypropylene or polyvinyl chloride) by a mold injection process. In an alternative implementation, the retaining collars 18 are attached to the proximal end 14 of filter frame 12 by crimping, soldering, bonding, or other suitable attachment means.

Coupled to the distal end 16 of filter frame 12 and extending proximally through lumen 42 of retaining collar 18 are expandable struts 20. Expandable struts 20 have a proximal section 22 and a distal section 24. The distal section 24 of expandable struts 20 is coupled to the distal end 16 of filter frame 12 at joint 46. The proximal section 22 of expandable struts 20, in turn, extends through lumen 42 of retaining collar 18 and terminates at a point proximate and proximal opening 44. In a preferred application, the proximal section 22 of expandable struts 20 is slidably disposed within lumen 42 formed by retaining collar 18.

Although the exemplary embodiment illustrated in FIG. 1 shows an embolic protection filter having two expandable struts 20 biased 180° apart from each other (as viewed from an end), any number of expandable struts may be employed. For example, an embolic protection filter in accordance with the present invention may include four expandable struts 20 circumferentially disposed 90° apart. In yet another example, an embolic protection filter in accordance with the present invention may include six expandable struts 20 circumferentially disposed 60° apart.

A pre-formed bend region 48 located along each of the expandable struts 20 between proximal sectional 22 and distal section 24 provides flexion between the sections 22, 24. Pre-formed bend region 48 biases each of the expandable struts 20 in an outward direction so that when unconstrained at the proximal end thereof, each of the expandable struts 20 radially expands towards the wall of the vessel. The bend region 48 may be offset along the length of each expandable strut 20 (if desired), or may be centrally located along the length each expandable strut 20.

The expandable struts 20 can be comprised of any number of suitable materials such as a 304 or 316 grade stainless steel, or polymeric materials such as polyvinylchloride (PVC) or polytetrafluoroethylene (PTFE). More preferably, the expandable struts 20 can be comprised of a shape-memory material such as nickel-titanium (NiTi) alloy. Nickel-titanium alloy exhibits pseudo-elastic capabilities at body temperature (37° C.), allowing it to endure a substantial amount of bending or flexing with relatively little residual strain. It is anticipated, however, that other biocompatible materials may be used.

A weld bead 50 disposed proximate the proximal section 22 of each expandable strut 20 prevents the proximal section 22 from detaching from the retaining collar 18. Weld bead 50 has an outer dimension that is greater than the inner diameter of lumen 42, thereby preventing distal movement of the weld bead beyond opening 44.

Attached to the distal section 24 of each expandable strut 20 is a filter mesh 26. Filter mesh 26 comprises a blood permeable sac furled about the distal section 24 of each expandable strut 20. In an open position, filter mesh 26 expands outwardly in the vessel, causing the dislodged embolic debris to collect within the sac.

To prevent the expandable struts 20 from expanding during transport of the embolic protection filter 10, an actuator mechanism 56 comprising a tubular member having a proximal end (not shown) and a distal end 60 can be used to actuate the expandable struts 20 between the collapsed, radially compact position and the open, radially expanded position. The distal end 60 of actuator mechanism 56 includes a channel 62, defined by a resilient portion of actuator mechanism 56, for temporarily locking the actuator mechanism 56 to each weld bead 50 to prevent the expandable struts 20 from deploying during transport.

Although channel 62 is shown in the exemplary embodiment of FIG. 1, it is to be recognized that other suitable locking mechanisms may be employed. For example, the proximal section 22 of each expandable strut 20 may include an enlarged outer diameter portion having a threaded surface adapted to engage a corresponding threaded surface disposed on the distal end 60 of actuator mechanism 56.

In the particular illustration of FIG. 1, embolic protection filter 10 is shown in the collapsed, radially compact position prior to deployment. The expandable struts 20 are constrained by applying a proximal force to actuator mechanism 56. The filter frame 12, in turn, is prevented from sliding proximally along the guidewire 34 by an advancing member 64 disposed proximal the proximal end 14 of filter frame 12. An optional hub (not shown) disposed about a proximal portion of the guidewire 34 can be utilized to prevent relative motion between the actuator mechanism 56 and the advancing member 64.

To actuate the embolic protection filter 10 within the vessel once placed distal a lesion, actuator mechanism 56 is retracted proximally while advancing member 64 is held stationary, causing the weld beads 50 to detach from the channel 62. When this occurs, the proximal section 22 of each expandable strut 20 slides distally through lumen 42 of retaining collar 18, causing each expandable strut 20 to radially expand towards the wall of the vessel, as shown in FIG. 3. As a result, filter mesh 26, which is furled about the distal section 24 of each expandable strut 20, is stretched across the diameter of the vessel to collect embolic debris dislodged during the procedure. After embolic protection filter 10 has been deployed, advancing member 64 can be retracted proximally along the guidewire 34 and removed from the body, or can be used to advance other intravascular devices along the guidewire 34.

Retrieval of the device from the body lumen subsequent to deployment is accomplished by reversing the aforesaid steps. To collapse the expandable struts 20, the operator slides the actuator mechanism 56 distally until weld balls 50 lock into channel 62. Once attached, the operator slides the actuator mechanism 56 proximally, causing the expandable struts 20 to collapse into the collapsed, radially compact position. Advancing member 64 can be used to prevent the embolic protection filter 10 from moving proximally during this process, if necessary.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood, however, that this disclosure is, in many respects, only illustrative. Changes may be made in details, particular in matters of shape, size and arrangement of parts without exceeding the scope of the invention.

What is claimed is:

1. An embolic protection filter comprising:
   a filter frame slidably and rotationally disposed along an elongate member, said filter frame having a proximal end and distal end;
   a plurality of retaining collars coupled to the proximal end of said filter frame;
   a plurality of expandable struts each having a proximal section and a distal section, the proximal section adapted to slide within the retaining collars, the distal section secured to the distal end of said filter frame, wherein, in use, said plurality of expandable struts are biased to radially expand from a collapsed, radially compact position to an open, radially expanded position;

a filter mesh coupled to said plurality of expandable struts for filtering embolic material; and an actuator mechanism adapted to engage the proximal section of the struts and configured to place tension on the struts.

2. The embolic protection filter of claim 1, wherein said plurality of expandable struts are self-expanding within a body lumen upon actuation.

3. The embolic protection filter of claim 1, further comprising an advancing member for advancing the embolic protection filter along the elongate member.

4. The embolic protection filter of claim 3, wherein said advancing member comprises a tubular member.

5. The embolic protection filter of claim 1, further comprising an object at the proximal end of each one of said plurality of expandable struts, said object adapted to prevent each one of said plurality of expandable struts from exiting the retaining collars.

6. The embolic protection filter of claim 5, wherein said object is a weld bead.

7. The embolic protection filter of claim 1, wherein said actuator means is a tubular member having a proximal end and a distal end, the distal end defining a channel adapted to releasably lock onto the proximal ends of the struts.

8. The embolic protection filter of claim 1, wherein said plurality of expandable struts are comprised of a shape-memory material.

9. The embolic protection filter of claim 8, wherein said shape-memory material is nickel-titanium alloy.

10. The embolic protection filter of claim 1, wherein each of said plurality of expandable struts has a pre-formed bend region adapted to bias said plurality of expandable struts in an outward direction.

11. The embolic protection filter of claim 10, wherein said preformed bend region is centrally located along the length of each of said plurality of expandable struts.

12. The embolic protection filter of claim 1, wherein said filter mesh is attached to the distal section of said plurality of expandable struts.

13. The embolic protection filter of claim 1, wherein said filter mesh comprises a blood permeable sac.

14. An embolic protection filter comprising:

a guidewire having a proximal end, a distal end, and a distal stop;

a filter frame slidably and rotationally disposed along the guidewire, said filter frame having a proximal end and a distal end;

a plurality of retaining collars coupled to the proximal end of said filter frame, each of said plurality of retaining collars defining a lumen;

a plurality of self-expanding struts each having a proximal section and a distal section, the proximal section adapted to slide within the lumen formed by a corresponding one of said plurality of retaining collars, the distal section secured to the distal end of said filter frame, wherein, in use, the plurality of self-expanding struts are biased to radially expand from a collapsed, radially compact position to an open, radially expanded position;

a filter mesh attached to the distal section of each one of said plurality of self-expanding struts, said filter mesh comprising a blood permeable sac;

an actuator mechanism for actuating said plurality of self expanding struts between the collapsed, radially compact position and the open, radially expanded position, the actuator mechanism adapted to engage the proximal section of the struts and configured to place tension on the struts; and an advancing member for advancing the embolic protection filter along the guidewire.

15. The embolic protection filter of claim 14, wherein said advancing member comprises a tubular member.

16. The embolic protection filter of claim 14, further comprising an object at the proximal end of each of said plurality of self-expanding struts, said object adapted to prevent said plurality of self-expanding struts from exiting the lumen formed by the corresponding retaining collar.

17. The embolic protection filter of claim 16, wherein said object is a weld bead.

18. The embolic protection filter of claim 16, wherein said actuator mechanism is a tubular member having a proximal end and a distal end, the distal end defining a channel adapted to releasably lock onto said object.

19. The embolic protection filter of claim 14, wherein said plurality of expandable struts are comprised of a shape-memory material.

20. The embolic protection filter of claim 19, wherein said shape-memory material is nickel-titanium alloy.

21. The embolic protection filter of claim 14, wherein each of said plurality of expandable struts has a pre-formed bend region adapted to bias said plurality of self-expanding struts in an outward direction.

22. The embolic protection filter of claim 21, wherein said pre-formed bend region is centrally located along the length of each of said plurality of self-expanding struts.

23. A method of filtering embolic material from a body lumen, comprising:

providing an embolic protection filter comprising a filter frame slidably and rotationally disposed along a guidewire, said filter frame having a proximal end and a distal end; a plurality of retaining collars coupled to the proximal end of said filter frame, a plurality of expandable struts each having a proximal section and a distal section, the proximal section adapted to slide within the lumen formed by a corresponding one of said plurality of retaining collars, the distal section secured to the distal end of said filter frame; and a filter mesh coupled to said plurality of expandable struts, and an actuator mechanism adapted to engage the proximal section of the struts and configured to place tension on the struts;

inserting the guidewire into a body lumen across a lesion;

advancing the embolic protection filter along the guidewire to a desired location distal the lesion;

actuating the plurality of expandable struts from a collapsed, radially compact position to an open, radially expanded position with the body lumen; and collecting dislodged embolic material within the body lumen.

24. A method of filter embolic material from a body lumen as in claim 23, further comprising the step of removing the embolic protection filter and collected embolic material from the body lumen.

25. The embolic protection filter of claim 1, wherein the actuator mechanism is configured to move the proximal end of the struts in the proximal direction relative to the filter frame.

26. The embolic protection filter of claim 25, wherein the filter is configured to move from an open position to a closed position when the actuator mechanism moves the proximal end of the struts in a proximal direction.

27. The embolic protection filter of claim 1, wherein the actuator mechanism is further adapted to push on the struts.

28. The embolic protection filter of claim 27, wherein the filter is configured to move from a closed position to an open position when the actuator mechanism pushes on the struts.

29. An embolic protection filter comprising:
   a filter frame slidably and rotationally disposed along an elongate member, said filter frame having a proximal end and distal end;
   a filter support structure that has an open position and a closed position and is predisposed to assume the open position;
   a filter mesh covering at least a portion of the filter support structure wherein the position of the filter support structure covered by the filter mesh is called the filter zone, wherein the filter zone has an outer surface; and
   an actuator mechanism adapted to engage a proximal section of the filter support structure and configured to place tension on the filter support structure, wherein the actuator mechanism is configured to move the proximal end of the filter support structure in the proximal direction relative to the filter frame.

30. The embolic protection filter of claim 29, wherein the filter support structure comprises a plurality of struts.

31. The embolic protection filter of claim 29, wherein a distal end of the filter support structure is attached to the filter frame.

32. The embolic protection filter of claim 29, the filter frame further comprising at least one collar at a proximal region of the filter frame.

33. The embolic protection filter of claim 32, wherein a proximal end of the filter support structure passes through the at least one collar.

34. The embolic protection filter of claim 29, wherein the filter is configured to move from an open position to a closed position when the actuator mechanism moves the proximal end of the filter support mechanism in a proximal direction relative to the filter frame.

35. The embolic protection filter of claim 29, wherein the actuator mechanism is further adapted to push on the filter support structure.

36. The embolic protection filter of claim 35, wherein the filter is configured to move from a closed position to an open position when the actuator mechanism pushes on the filter support structure.

37. The embolic protection filter of claim 29, wherein the embolic protection filter is configured to be actuated between open to closed positions while maintaining the outer surface in an unconstrained state.

38. The embolic protection filter of claim 29, wherein the embolic protection filter is configured to be delivered and deployed while maintaining the outer surface in an unconstrained state.

39. The embolic protection filter of claim 29 wherein the embolic protection filter is configured to be retrieved from a patient's vasculature while maintaining the outer surface in an unconstrained state.

* * * * *